United States Patent [19]

Steen

[11] Patent Number: 4,737,025
[45] Date of Patent: Apr. 12, 1988

[54] FLOW CHAMBER DEVICE FOR FLOW CYTOMETERS

[76] Inventor: Harald Steen, Wolffsgt. 3, N-0358 Oslo 3, Norway

[21] Appl. No.: 36,675
[22] PCT Filed: Jul. 10, 1986
[86] PCT No.: PCT/NO86/00050
§ 371 Date: Mar. 5, 1987
§ 102(e) Date: Mar. 5, 1987
[87] PCT Pub. No.: WO87/00282
PCT Pub. Date: Jan. 15, 1987

[30] Foreign Application Priority Data
Jul. 10, 1985 [NO] Norway ................. 852761

[51] Int. Cl.⁴ .............. G01N 33/48; G01N 21/49; G01N 21/64
[52] U.S. Cl. ........................... 356/39; 356/72; 356/73
[58] Field of Search ................. 356/38, 39, 72, 73

[56] References Cited
U.S. PATENT DOCUMENTS
4,225,229 9/1980 Gönde ................. 356/39
4,408,877 10/1983 Lindmo et al. ....... 356/39 X
4,426,154 1/1984 Steen ................... 356/73

Primary Examiner—Vincent P. McGraw
Attorney, Agent, or Firm—Cushman, Darby & Cushman

[57] ABSTRACT

The present invention relates to a device which facilitates that biological cells and other microscopical particles, carried by a microscopial laminar fluid flow, are brought one by one across the open surface of a plane glass with a velocity which may be varied from above 30 m/sec. to below 1 cm/sec., so that the fluorescence and light scattering of the cells/particles may be measured through optics situated on each side of the plane glass. The device comprises a nozzle (1) with hydrodynamic focusing having its axis at an oblique angle to said glass surface. Furthermore, at the same time the electrical volume of the cells/particles may be determined by means of an electrode, made of inert metal, situated in the contact plane between the nozzle (1) and said glass (2) and an electrode situated in the fluid supply (8) of the nozzle (1). By retaining a constant electrolytical current between the electrode (6) and the electrode (7) the electrical volume of the cells/particles may be measured by the voltage pulses produced between the said electrodes when the cells/particles pass through the orifice.

8 Claims, 2 Drawing Sheets

FLOW CHAMBER DEVICE FOR FLOW CYTOMETERS

The present invention concerns a device which is a flow chamber to be employed in flow cytometers. This device facilitates that the biological cells or other microscopical particles, carried by a microscopical laminar flow of fluid, are brought one by one across the open surface of a plane glass with a velocity which may be varied from above 30 m/sec. to below 1 cm/sec., so that the fluorescence and light scattering of the cells/particles may be measured through optics situated on each side of the plane glass. A further development of the device facilitates that the electrical volume of the cells/particles may be measured simultaneously.

The function of the flow chamber in such instruments is to make particles or biological cells to flow one by one in a highly reproducible manner through the measuring area of the instrument.

The intention of the present invention is to facilitate considerably lower flow velocity and a corresponding increase in the detection sensitivity as compared to other types of flow chambers and furthermore to facilitate the measurement of the electrical volume of the particles/cells simultaneously with meaurement of the photometrical signals.

Flow cytometers are instruments for the measurement of the fluorescence and light scattering properties of microscopical particles. The measurement is carried out when the particles, carried by a laminar flow of fluid of microscopical dimensions, pass one by one through the focus of a beam of excitation light. The pulse of fluorescence emitted by each particle when it passes through this focus is determined by the chemical composition of the particle and is characteristic of this composition. The pulses of fluorescence are detected through appropriate optics by a photoelectric detector which transforms the pulses of fluorescence to equivalent electrical pulses. These pulses are transferred to a multichannel pulse height analyzer (MCA) which measures the size of the pulses and thereby produces a histogram showing the number of particles as a function of fluorescence intensity.

The light which is scattered by each particle when it passes through the focus of excitation light, and which is determined by the structure and the size of the particle, is detected in a similar manner by another detector and thus gives rise to a histogram which characterizes the particles with regard to structure and size.

The fluid flow in a flow cytometer may have a typical velocity of about 20 m/sec., and the excitation focus which constitutes the measuring area of the instrument may have a size of about 50 $\mu$m. This means that each particle is measured in about 3 $\mu$sec., which in turn means that it is possible to measure several thousand particles per second. The smallest amount of fluorescent material per particle which may be detected is about $1 \cdot 10^{-16}$ g. Particle sizes below $1 \cdot 10^{-2}$ $\mu$m$^3$ may be measured by light scattering. Both fluorescence and light scattering may be measured with a precision of about 1%. The most common use of flow cytometers has so far been measurement of the size of biological cells and their content of essential components such as DNA, enzymes and other proteins.

The flow chamber is a critical component in all flow cytometers because the stability of the particle flow with regard to position as well as velocity determines the precision of the measurement. In order to achieve high stability most flow chamber employs hydrodynamic focusing of the particles. Hydrodynamic focusing is achieved when the carrying fluid is forced throgh the microscopical orifice of a conical nozzle so that a laminar jet of fluid is produced. The particles are introduced in the carrying fluid through a thin cylindrical tube having its axis in common with that of the nozzle and its opening where the nozzle diameter is much larger than the diameter of the cylindrical tube. Thus, the particles will be centered in the microscopical jet which leaves the nozzle.

In one type of flow chambers the free jet produced by the nozzle is used as measuring region in the flow cytometer. In such instruments the excitation light is preferably produced by a laser. In another type of flow chamber the fluid flow is confined to a straight cylindrical or rectangular tube passing through the measuring area. In a third type of flow cytometers, which emloys a conventional high pressure arc lamp as the source of excitation light, this tube has a more complicated shape.

It is of critical importance that the flow chamber has optical properties which makes the fluorescence and the light scattering of the flow chamber itself as low as possible in order to achieve the highest possible signal to noise ratio.

Previously, a flow chamber was developed which may be adapted to a fluorescence microscope with incident illumination (epi illumination) through oil immersion optics with high numerical aperture (N.A.=1.3) which thereby gives optimal intensity of excitation and detection of fluorescence. In this flow chamber the free jet from a nozzle with hydrodynamic focusing falls at an oblique angle on to the open surface of microscope cover glass thereby producing a laminar flow across the surface of the glass, with the particles confined to a narrow sector of this flow (Norwegian Pat. No. 144002). The other side of this cover glass is optically coupled through the oil immersion objective of the fluorescence microscope. The measuring area of this instrument, that is, the focus of the microscope, thus constitutes a microscopical region of the fluid flow adjacent to the surface of the cover glass. The liquid is drained from the cover glass by suction through a thin tube, the opening of which touches the glass surface. The fluid flow across the surface of the cover glass is thus confined between the surface of the cover glass on the one side and it free surface against the open atmosphere on the other. This configuration has a minimal number of optical surfaces which may scatter light. Furthermore, these surfaces are approximately plane and are situated at right angle to the optical axis of the microscope. This gives this type of flow chamber exceptionally low light scattering and fluorescence and a correspondingly high signal to noise ratio in the measurement of particles. The open configuration of this type of flow chamber has the further advantage that it is very simple to clean.

The amount of fluorescence and scattered light from a particle passing through the measuring area of the flow cytometer is proportional to the time spent by the particle in the measuring area and thus inversely proportional to the velocity of the flow. The sensitivity of the flow cytometer is therefore inversely proportional of the flow cytometer is therefore inversely proportional to the flow velocity. By reducing this velocity it is possible to increase the sensitivity of the instrument correspondingly. In the previous flow chamber (NO-PS No. 144002) the nozzle produces a microscopical jet of water in air. In order for the flow chamber to function according to its purpose the laminarity of the jet must be conserved until the jet hits the surface of the cover glass. The condition that such a nozzle shall produce a laminar jet is that the velocity exceeds a certain minimum value given by:

$$v_{min} = 2(2\sigma/d\cdot\rho)^{\frac{1}{2}} \quad (1)$$

where $\sigma$ is the surface tension of the fluid, $\rho$ the density of the liquid and d the orifice diameter. This condition limits the sensitivity of all flow cytometers where the cells/particles are carried through the measuring area by a jet in air.

For a nozzle orifice having a diameter of 70 $\mu$m, which is a typical value for flow cytometer nozzles, $v_{min} = 3$ m/sec., while the typical flow velocity is about 10 m/sec. This means that the sensitivity of the instrument can not be increased by more that a factor of 3 by reducing the flow velocity. One major purpose of the present invention is to facilitate a much larger reduction of the flow velocity and thereby a corresponding increase of the detection sensitivity.

Another main purpose is to facilitate measurement of the electrical volume of the particles simultaneously with the measurement of fluorescence and light scattering. A method for measuring the volume of microscopical particles has been known and used for many years. In this method the particles are passed through an opening of microscopical size, e.g. 100 $\mu$m diameter, which is filled by an electrolyte, e.g. physiological salt solution. On each side of this opening is situated an electrode and between these electrodes, that is, through the opening, a constant electrical current is maintained. The voltage between these electrodes will thus be determined by the electrolytical resistance of the opening. When a particle, which is not electrically conductive, passes through the opening this resistance will increase in proportion to the volume of the particle. The passage of the particle through the opening will thus give rise to a voltage pulse between the electrodes which is proportional to the volume of the particle. Such measurement of the volume of biological cells has proved to be quite useful in combination with the measurement of fluorescence and light scattering in flow cytometers. In the flow chamber mentioned above, as well as other flow systems where the nozzle produces a jet in air, such meaurement is not possible.

The characteristics of the said device are evident primarily from the following claims 1 and 2. Further characteristics of the device according to the invention are evident from the other claims as well as from the following description referring to the included drawings.

Figure 1:
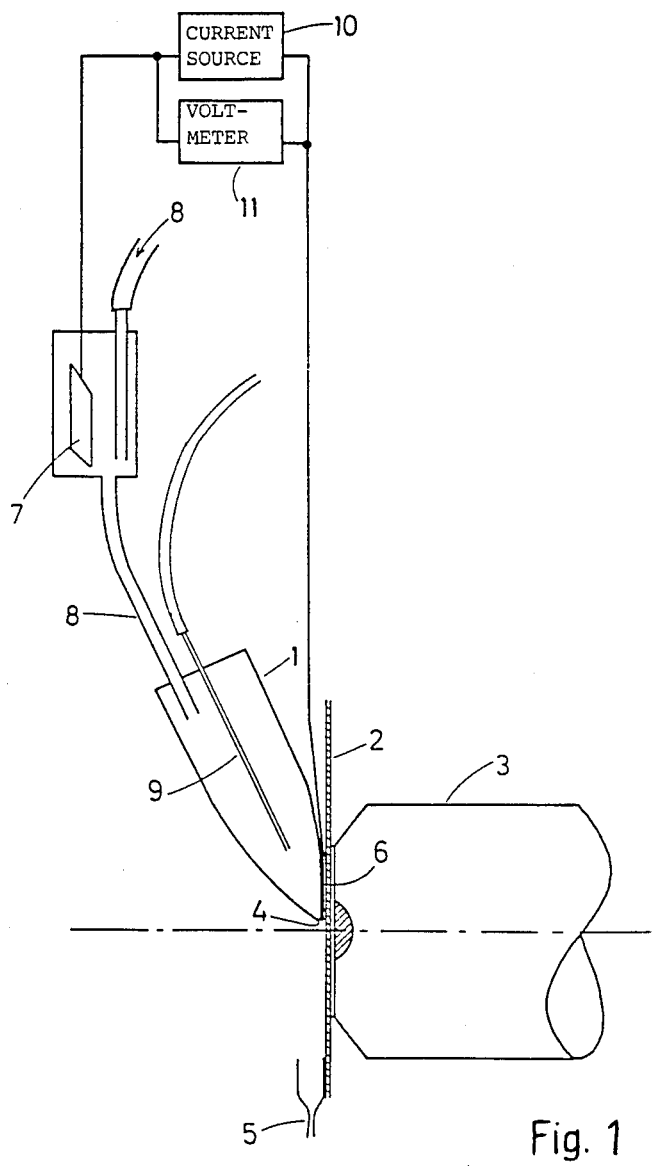
FIG. 1 illustrates schematically the device according to the invention.
Figure 2:
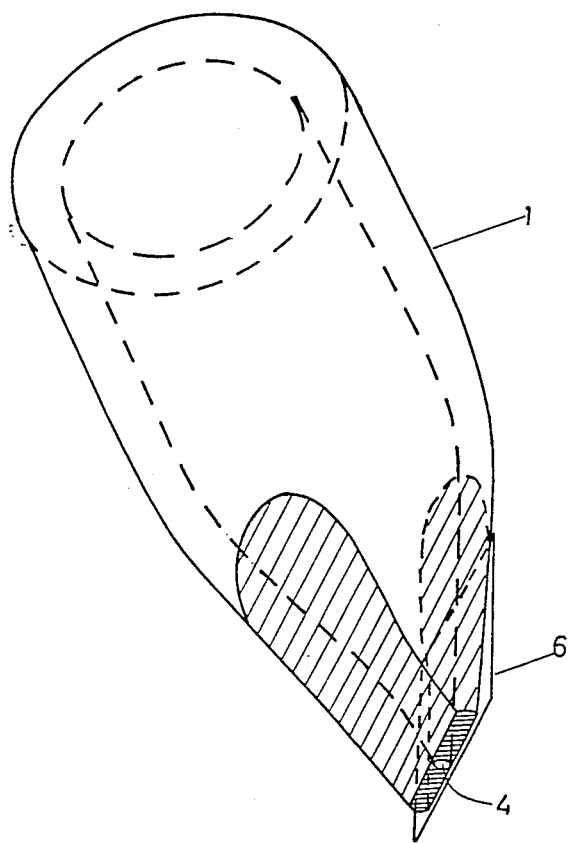
FIG. 2 illustrates the nozzle which is part of the device according to the invention.

In the present invention is employed a nozzle 1 with hydrodynamic focusing. The nozzle forms a laminar fluid flow across the open surface of a cover glass 2, the other side of which is coupled optically to microscope optics 3. In the present invention, however, the nozzle is formed so that its orifice 4 comes into direct contact with the glass surface 2 (FIG. 1). Hence, the flow from the nozzle does not form a jet in air but rather a fluid meniscus which connects the orifice 4 with the glass surface. In order to give the meniscus a flat form as close to the orifice as possible, which is of critical importance for its optical properties, the nozzle is formed so that its tip has a flat cross section (FIG. 2) the height of which just exceeds the orifice diameter, while the width is several times the height. The nozzle is situated so that one of its plane sides rests against the surface of the cover glass.

Thus, one of the main intentions of the invention is achieved, viz. that the limiting velocity given by equation 1 no longer is a condition for the laminarity of the flow from the nozzle. Experiments show that with this device laminarity can be maintained at least down to velocities of the order of 1 cm/sec., that is a reduction in flow velocity and a corresponding increase in sensitivity, of approximately a factor of 100 as compared to what was possible in our previous flow chamber. The condition for maintaining a stable laminar flow on the surface of the cover glass at these low velocities is that the cover glass 2 is situated vertically so that the fluid runs in the direction of the gravity. A tube 5 conducts the fluid away from the cover glass 2.

The other main purpose of the invention, that is the measurement of electrical volume, is achieved by a platinum electrode 6 (thickness 10 $\mu$m) which is situated between the nozzle and the cover glass surface. Through the meniscus which connects the glass surface with the nozzle orifice this electrode is electrically connected with the other electrode 7 which is situated in the fluid supply 8 of the nozzle 1 (FIG. 1). By maintaining a constant electrolytical current from a current source 10 between the two electrodes it is possible to determine the electrical volume of the particles passing through the orifice by measuring the voltage pulses between the electrodes caused by the particles by means of the voltage meter 11.

The present invention has two other important advantages as compared to our previous flow chamber: Firstly, the low flow velocities make it possible to record images of cells/particles as they pass through the measuring region. The photometrical signals from a cell/particle may thus trigger: (1) a light pulse from an appropriate light source, e.g. a laser, which is focused in the measuring region, and (2) an electronic camera. Secondly, the present invention implies that the distance between the nozzle orifice and the surface of the cover glass is perfectly constant, thus increasing the precision of the path of the particles/cells through the measuring region

I claim:

1. A flow chamber device to be employed in a flow cytometer facilitating that biological cells or particles, carried by a microscopical laminar fluid flow, are brought one by one across the open surface of a plane glass with a velocity which may be varied from above 30 m/sec. to below 0.01 m/sec. (1 cm/sec.), so that the fluorescence and light scattering of the cells/particles may be measured through optics situated on each side of the plane glass, characterized by the fact that the flow chamber comprises a nozzle (1) situated in contact with the open surface of a plane glass (2) having its axis at an oblique angle to the said glass (2) so that the orifice of the nozzle (4) is situated immediately adjacent to the glass surface and so that the flow from the orifice of the nozzle (4) connects this orifice with the glass surface through a meniscus of fluid maintained independently of the flow velocity.

2. A device according to 1, characterized in that the tip of the nozzle (1) has two opposite plane sides so that the cross section of the said tip has a height just exceeding the diameter of the orifice of the nozzle (4) and a width which is several times larger than said height.

3. A device according to claim 1, characterized in that the nozzle (1) rests against the cover glass (2) with one of the plane surfaces of the tip of the nozzle.

4. A device according to claim 1 characterized in that a carrying fluid is introduced in the nozzle (1) so that it runs in a laminar fashion toward the conical orifice (4) while the cells/particles are introduced into the nozzle so that the cells/particles are confined to the central part of the cross section of the flow where it leaves the nozzle orifice (4) and thus confined to a narrow sector of the flow on the surface of the glass (2).

5. A device according to claim 1 characterized in that the glass (2) is situated vertically so that the flow on the glass surface moves in the direction of the gravity.

6. A device according to claim 1 characterized in that a tube (5) is situated at the lower part of said glass (2) thus draining the fluid away from the flow chamber.

7. A device according to claim 1 characterized in that the other side of the glass (2) may be optionally coupled to a microscope (3) having Epi-illumination, in such a way that the particle path across the surface of the glass (2) passes through the microscope focus.

8. A flow chamber device to be employed in a flow cytometer facilitating that biological cells or particles, carried by a microscopical laminar fluid flow are brought one by one across the open surface of a plane glass with a velocity which may be varied from above 30 m/sec. to below 0.01 m/sec. (1 cm/sec.), so that the fluorescence and light scattering of the cells/particles may be measured through optics situated on each side of the plane glass while at the same time the electrical volume of the cells/particles can be determined, characterized by the fact that the flow chamber comprises a nozzle (1) situated in contact with the open surface of a plane glass (2) having its axis at an oblique angle to the said glass (2) so that the orifice of the nozzle (4) is situated immediately adjacent to the glass surface and so that the fluid flow from the nozzle orifice (4) connects the orifice with the glass surface through a meniscus of fluid which is maintained independently of the flow velocity, and that the electrical volume of the cells/particles is determined by means of an electrode (6) of inert metal situated in the plane of contact between said glass (2) and said nozzle (1), while an electrode (7) is situated in the fluid supply (8) of the nozzle (1) so that a constant electrolytical current between said electrodes (6) and (7) is maintained through the nozzle orifice (4) in order to facilitate measurement of the electrical volume of the particles passing through the orifice (4) of said nozzle (1).

* * * * *